US012004849B2

(12) United States Patent
Koyrakh et al.

(10) Patent No.: US 12,004,849 B2
(45) Date of Patent: Jun. 11, 2024

(54) SYSTEMS, METHODS, AND COMPUTER-READABLE MEDIA FOR NON-RIGID REGISTRATION OF ELECTROMAGNETIC NAVIGATION SPACE TO CT VOLUME

(71) Applicant: Covidien LP, Mansfield, MA (US)

(72) Inventors: Lev A. Koyrakh, Plymouth, MN (US); Ron Barak, Herzliya (IL); Oren P. Weingarten, Herzliya (IL); Alexander Nepomniashchy, Haifa (IL)

(73) Assignee: Covidien LP, Mansfield, MA (US)

( * ) Notice: Subject to any disclaimer, the term of this patent is extended or adjusted under 35 U.S.C. 154(b) by 821 days.

(21) Appl. No.: 16/211,314

(22) Filed: Dec. 6, 2018

(65) Prior Publication Data

US 2019/0175061 A1 Jun. 13, 2019

Related U.S. Application Data

(60) Provisional application No. 62/597,293, filed on Dec. 11, 2017.

(51) Int. Cl.
*A61B 5/06* (2006.01)
*A61B 1/267* (2006.01)
(Continued)

(52) U.S. Cl.
CPC ............ *A61B 5/066* (2013.01); *A61B 1/2676* (2013.01); *A61B 5/062* (2013.01); *A61B 5/7253* (2013.01);
(Continued)

(58) Field of Classification Search
CPC ......... A61B 5/066; A61B 34/20; A61B 6/032; A61B 5/062; A61B 5/7253; A61B 1/2676;
(Continued)

(56) References Cited

U.S. PATENT DOCUMENTS 5,727,554 A 3/1998 Kalend et al.
6,076,005 A 6/2000 Sontag et al.
(Continued)

FOREIGN PATENT DOCUMENTS

JP 2006512950 A 4/2006
WO 2011101754 A1 8/2011

OTHER PUBLICATIONS

International Search Report and Written Opinion of PCT application No. PCT/US2018/064840 dated Apr. 1, 2019.
(Continued)

*Primary Examiner* — Jonathan Cwern
(74) *Attorney, Agent, or Firm* — Weber Rosselli & Cannon LP

(57) ABSTRACT

Methods, systems, and computer-readable media for registering electromagnetic navigation data of a luminal network to a 3D model of the luminal network includes accessing a 3D model of a luminal network based on computed tomographic (CT) images of the luminal network, the 3D model corresponding to a CT coordinate space, selecting a plurality of reference points within the 3D model of the luminal network, accessing a plurality of survey points within the luminal network, the plurality of survey points being based on electromagnetic navigation data and corresponding to a body coordinate space, correlating the plurality of reference points and the plurality of survey points to determine pairs of correlated reference points and survey points; and deriving a transformation that maps the body coordinate space to the CT coordinate space based on the pairs of correlated reference points and survey points.

18 Claims, 6 Drawing Sheets

(51) Int. Cl.
*A61B 5/00* (2006.01)
*A61B 6/00* (2006.01)
*A61B 6/03* (2006.01)
*A61B 6/50* (2024.01)
*A61B 17/00* (2006.01)
*A61B 34/10* (2016.01)
*A61B 34/20* (2016.01)
*A61B 90/00* (2016.01)
*G06T 7/30* (2017.01)

(52) U.S. Cl.
CPC .............. *A61B 6/032* (2013.01); *A61B 34/20* (2016.02); *G06T 7/30* (2017.01); *A61B 6/504* (2013.01); *A61B 6/5247* (2013.01); *A61B 6/547* (2013.01); *A61B 2017/00809* (2013.01); *A61B 2034/105* (2016.02); *A61B 2034/2051* (2016.02); *A61B 2034/2072* (2016.02); *A61B 2090/363* (2016.02); *A61B 2090/364* (2016.02); *A61B 2090/3925* (2016.02)

(58) Field of Classification Search
CPC .............. A61B 6/547; A61B 2034/105; A61B 2090/3925; A61B 2090/363; A61B 2034/2051; A61B 6/504; A61B 2017/00809; A61B 2034/2072; A61B 6/5247; A61B 2090/364; G06T 7/30; G06T 2207/10081; G06T 2207/30061; G06T 7/33
See application file for complete search history.

(56) References Cited

U.S. PATENT DOCUMENTS

| | | | |
|---|---|---|---|
| 6,144,875 A | 11/2000 | Schweikard et al. | |
| 6,188,355 B1 | 2/2001 | Gilboa | |
| 6,373,916 B1 | 4/2002 | Inoue et al. | |
| 6,473,634 B1 | 10/2002 | Barni | |
| 6,473,635 B1 | 10/2002 | Rasche | |
| 6,501,981 B1 | 12/2002 | Schweikard et al. | |
| 6,580,938 B1 | 6/2003 | Acker | |
| 6,865,253 B2 | 3/2005 | Blumhofer et al. | |
| 7,123,758 B2 | 10/2006 | Jeung et al. | |
| 7,213,820 B2 | 5/2007 | Drummond | |
| 7,233,280 B2 | 6/2007 | Mor et al. | |
| 7,318,805 B2 | 1/2008 | Schweikard et al. | |
| 7,403,638 B2 | 7/2008 | Jeung et al. | |
| 7,551,759 B2 | 6/2009 | Hristov et al. | |
| 7,853,308 B2 | 12/2010 | Sauer et al. | |
| 7,916,918 B2 | 3/2011 | Suri et al. | |
| 8,200,315 B2 | 6/2012 | Mostafavi | |
| 8,233,688 B2 | 7/2012 | Soubelet et al. | |
| 8,295,435 B2 | 10/2012 | Wang et al. | |
| 8,331,532 B2 | 12/2012 | Nord et al. | |
| 8,482,606 B2 | 7/2013 | Razzaque et al. | |
| 8,577,177 B2* | 11/2013 | Guetter ................. | G06T 3/0068 382/294 |
| 8,625,869 B2 | 1/2014 | Harder et al. | |
| 8,744,045 B2 | 6/2014 | Nord et al. | |
| 9,433,390 B2 | 9/2016 | Nathaniel et al. | |
| 9,833,167 B2 | 12/2017 | Cohen et al. | |
| 9,888,898 B2 | 2/2018 | Imagawa et al. | |
| 10,127,629 B2 | 11/2018 | Razzaque et al. | |
| 10,130,316 B2 | 11/2018 | Funabasama et al. | |
| 10,674,970 B2 | 6/2020 | Averbuch et al. | |
| 2004/0174437 A1* | 9/2004 | Dai ....................... | G06T 3/4084 348/222.1 |
| 2005/0182295 A1 | 8/2005 | Soper et al. | |
| 2008/0240536 A1 | 10/2008 | Soubelet et al. | |
| 2009/0227861 A1 | 9/2009 | Ganatra et al. | |
| 2011/0085720 A1 | 4/2011 | Averbuch | |
| 2011/0150274 A1* | 6/2011 | Patwardhan ........... | G06T 7/251 382/209 |
| 2012/0039519 A1* | 2/2012 | Fei ........................ | A61B 6/482 382/131 |
| 2012/0172712 A1 | 7/2012 | Bar-Tal | |
| 2012/0288173 A1 | 11/2012 | Rai et al. | |
| 2013/0259349 A1* | 10/2013 | Averbuch ................ | G06T 15/08 382/131 |
| 2014/0046315 A1 | 2/2014 | Ladtkow et al. | |
| 2014/0270441 A1 | 9/2014 | Baker | |
| 2014/0281961 A1 | 9/2014 | Baker | |
| 2014/0282216 A1 | 9/2014 | Baker | |
| 2015/0073266 A1 | 3/2015 | Brannan et al. | |
| 2015/0141858 A1 | 5/2015 | Razavi et al. | |
| 2016/0000356 A1 | 1/2016 | Brown et al. | |
| 2017/0112411 A1 | 4/2017 | Costello et al. | |
| 2017/0265947 A1* | 9/2017 | Dyer ..................... | A61B 6/501 |
| 2017/0294018 A1 | 10/2017 | Averbuch et al. | |
| 2018/0200002 A1* | 7/2018 | Kostrzewski .......... | G02C 7/049 |

OTHER PUBLICATIONS

Extended European Search Report issued in European application No. 18888876.2 dated Jul. 19, 2021.

* cited by examiner ns or coordinates in one space to locations or coordinates in another space. In order to perform such registration, several methods have been developed. One method, known as manual registration, is based on the visual identification with the bronchoscope of the main airways branching points and associating them with the points visually identified on the CT scans. During the registration procedure the user navigates the bronchoscope with catheter fitted with the magnetic sensing coil to the branching points in the airways and manually creates the associations between the branching points and the locations in the magnetic navigation space. Another method, known as automatic registration, is based on collection of the point cloud from the airways (called survey) using a catheter with the magnetic sensor at its tip, and then fitting the survey to the image of the airway tree derived from the CT scan using a segmentation algorithm. The details of such a system are described in commonly owned U.S. Patent Publication No. 2011/0085720, entitled AUTOMATIC REGISTRATION TECHNIQUE, filed on May 14, 2010, by Averbuch the entire contents of which are incorporated herein by reference.

SYSTEMS, METHODS, AND COMPUTER-READABLE MEDIA FOR NON-RIGID REGISTRATION OF ELECTROMAGNETIC NAVIGATION SPACE TO CT VOLUME

CROSS REFERENCE TO RELATED APPLICATION

The present application claims the benefit of and priority to U.S. Provisional Application Ser. No. 62/597,293, filed on Dec. 11, 2017, the entire contents of which are incorporated herein by reference.

BACKGROUND

Technical Field

The present disclosure relates to bronchial registration and, more particularly, to devices, systems, methods, and computer-readable media for automatically registering a three-dimensional (3D) electromagnetic navigation of a patient's airways with a 3D model generated from computed tomographic (CT) scan of the patient's airways.

Description of Related Art

A common device for inspecting the airway of a patient is a bronchoscope. Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools, therapeutic instruments can be inserted.

Bronchoscopes, however, are limited in how far they may be advanced through the airways due to their size. Where the bronchoscope is too large to reach a target location deep in the lungs, a clinician may utilize certain real-time imaging modalities such as computed tomography or fluoroscopy. Fluoroscopic images, while useful, present certain drawbacks for navigation as it is often difficult to distinguish luminal passageways from solid tissue. Moreover, the images generated are two-dimensional whereas navigating the airways of a patient requires the ability to maneuver in three dimensions.

Systems have been developed that enable the development of 3D models of the airways or other luminal networks, typically from a series of CT images. One such system has been developed as part of the ILOGIC® ELECTROMAGNETIC NAVIGATION BRONCHOSCOPY® (ENB™), system currently sold by Medtronic PLC. The details of such a system are described in commonly assigned U.S. Pat. No. 7,233,820, entitled ENDOSCOPE STRUCTURES AND TECHNIQUES FOR NAVIGATING TO A TARGET IN BRANCHED STRUCTURE, filed on Mar. 29, 2004, by Gilboa, the entire contents of which are incorporated herein by reference.

During the ENB procedures it is important to register the locations obtained during electromagnetic navigation to locations in the model generated from the CT scan. As understood in the art, "registration" refers to a translation, mapping, transformation, or the like, which converts locations or coordinates in one space to locations or coordinates While the system as described in U.S. Pat. No. 7,233,820 and U.S. Patent Publication No. 2011/0085720 are quite capable, there is always a need for development of improvements and additions to such systems.

SUMMARY

Provided in accordance with the present disclosure are devices, systems, methods, and computer-readable media for registering electromagnetic navigation data from a patient's airways with a 3D model of the patient's airways generated from CT images of the patient's airways.

In an aspect of the present disclosure, a method of registering electromagnetic navigation data of a luminal network to a 3D model of the luminal network is disclosed. The method includes: accessing a 3D model of a luminal network based on computed tomographic (CT) images of the luminal network, the 3D model corresponding to a CT coordinate space, selecting a plurality of reference points within the 3D model of the luminal network, accessing a plurality of survey points within the luminal network, the survey points being based on electromagnetic navigation data and corresponding to a body coordinate space, correlating the reference points and the survey points to determine pairs of correlated reference points and survey points, and deriving a transformation that maps the body coordinate space to the CT coordinate space based on the pairs of correlated reference points and survey points. In another aspect of the present disclosure, the luminal network is an airway of a patient, and the 3D model is a model of the airway of the patient.

In a further aspect of the present disclosure, the method includes selecting fiducial points from the plurality of survey points and the plurality of reference points. In yet another aspect, the method, in correlating the reference points with the survey points, includes matching the fiducial points selected from the plurality of survey points with the fiducial points selected from the plurality of reference points, where the pairs of correlated reference points and survey points include the matched fiducial points. In another embodiment of the present disclosure, correlating the reference points with the survey points is based on an inverse registration of the CT coordinate space to the body coordinate space. In a further aspect of the present disclosure, the inverse registration is one or more of an inverse of an optimized zone registration or an inverse of a multi-rigid registration. In yet another aspect of the present disclosure, the transformation that maps the body coordinate space to the CT coordinate space is a thin plate splines transformation.

In a further aspect of the present disclosure, the method includes updating the transformation during electromagnetic navigation of the luminal network by: obtaining further survey points, determining a registration of the body coordinate space to the CT coordinate space based on the further survey points, matching the further survey points with the plurality of reference points based on the registration, and updating the transformation based on the matching.

In a further aspect of the present disclosure, a system for registering electromagnetic navigation data to a 3D model of a luminal network is disclosed. The system includes a location sensor capable of being navigated within a luminal network inside a patient's body, an electromagnetic field generator configured to detect the location of the location sensor as it is navigated within the luminal network, a computing device including a processor and a memory, and an application stored in the memory and executed by the processor. The application, when executed, causes the computing device to access a 3D model of the luminal network based on computer tomographic (CT) images of the luminal network, the 3D model corresponding to a CT coordinate space, select a plurality of reference points within the 3D model of the luminal network, access a plurality of survey points within the luminal network, the survey points being based on locations of the location sensor while the location sensor is navigated within the luminal network, correlate the plurality of survey points with the plurality of reference points to determine pairs of correlated reference points and survey points, and derive a transformation that maps the body coordinate space to the CT coordinate space based on the pairs of correlated reference points and survey points. In various embodiments, the luminal network is an airway of a patient, and the 3D model is a model of the airway of the patient.

In various embodiments, the application, when executed, further causes the computing device to select fiducial points from the survey points and from the reference points. In various embodiments, in correlating the survey points with the reference points, the application, when executed, further causes the computing device to match the fiducial points selected from the survey points with the fiducial points selected from the reference points, where the pairs of correlated reference points and survey points include the matched fiducial points.

In various embodiments, correlating the survey points and the reference points is based on an inverse registration of the CT coordinate space to the body coordinate space. In various embodiments, the inverse registration is one or more of an inverse of an optimized zone registration or an inverse of a multi-rigid registration.

In various embodiments, the transformation that maps the body coordinate space to the CT coordinate space is a thin plate splines transformation. In various embodiments, the application stored in the memory, when executed, further causes the computing device to update the transformation during electromagnetic navigation of the luminal network by: obtaining further survey points, determining a registration of the body coordinate space to the CT coordinate space based on the further survey points, matching the further survey points with the reference points based on the registration, and updating the transformation based on the matching.

In a further aspect of the disclosure, a system for registering electromagnetic navigation data to a 3D model of a luminal network includes a computing device including a processor and a memory, and an application stored in the memory and executed by the processor. The application, when executed, causes the computing device to access a 3D model of a luminal network inside a patient's body where the 3D model is based on computed tomographic (CT) images of the luminal network and corresponds to a CT coordinate space, select a plurality of reference points within the 3D model of the luminal network, access a plurality of survey points within the luminal network where the plurality of survey points corresponds to a body coordinate space and is based on locations of a location sensor while the location sensor is navigated within the luminal network, correlate the plurality of reference points and the plurality of survey points to determine a plurality of correlated points, perform an inverse registration of the CT coordinate space to the body coordinate space based on the plurality of correlated points, interpolate a plurality of additional correlated points based on the inverse registration, and derive a transformation that maps the body coordinate space to the CT coordinate space based on the plurality of correlated points and the plurality of additional correlated points.

In a further aspect of the disclosure, a system for registering electromagnetic navigation data of a luminal network to a 3D model of the luminal network includes a computing device including a processor and a memory, and an application stored in the memory and executed by the processor. The application, when executed, causes the computing device to access a 3D model of a luminal network inside a patient's body where the 3D model is based on computed tomographic (CT) images of the luminal network and corresponds to a CT coordinate space, select a plurality of reference points within the 3D model of the luminal network, access a plurality of survey points within the luminal network where the plurality of survey points is based on electromagnetic navigation data and corresponds to a body coordinate space, perform an inverse registration of the CT coordinate space to the body coordinate space based on the plurality of reference points and the plurality of survey points, and derive a transformation that maps the body coordinate space to the CT coordinate space based on the inverse registration.

Any of the above aspects and embodiments of the present disclosure may be combined without departing from the scope of the present disclosure.

BRIEF DESCRIPTION OF THE DRAWINGS

Objects and features of the presently disclosed system and method will become apparent to those of ordinary skill in the art when descriptions of various embodiments thereof are read with reference to the accompanying drawings, wherein.

DETAILED DESCRIPTION

The present disclosure is directed to devices, systems, methods, and computer-readable media for registering electromagnetic (EM) navigation of a patient's airways with a 3D model of the patient's airways generated from CT scans. "Registration" refers to a translation, mapping, transformation, or the like, which converts locations or coordinates in one space to locations or coordinates in another space. The present disclosure provides registration accuracy by incorporating the flexibility of the lungs into the registration via the use of interpolation techniques, such as the Thin Plate Splines (TPS) Transformation, which is described below herein. Due to the flexibility of the lungs, the actual shape of the lungs during the time of a surgical procedure can be different from that at the time of the CT scan, resulting in the reduction of navigation accuracy. The TPS Transformation is a transformation which maps points from a CT space defined by a 3D model generated from CT scan data, to a body space defined by sensor readings during an electromagnetic navigation of a patient's airways. Because the TPS Transformation is used to convert between points in the CT space and in the body space, the transform can conversely be "fitted" to known pairings of points in the CT space and in the body space. As described in more detail below, deriving the TPS Transformation is performed using what are referred to herein as fiducial points and multi-rigid transformation.

Figure 1:
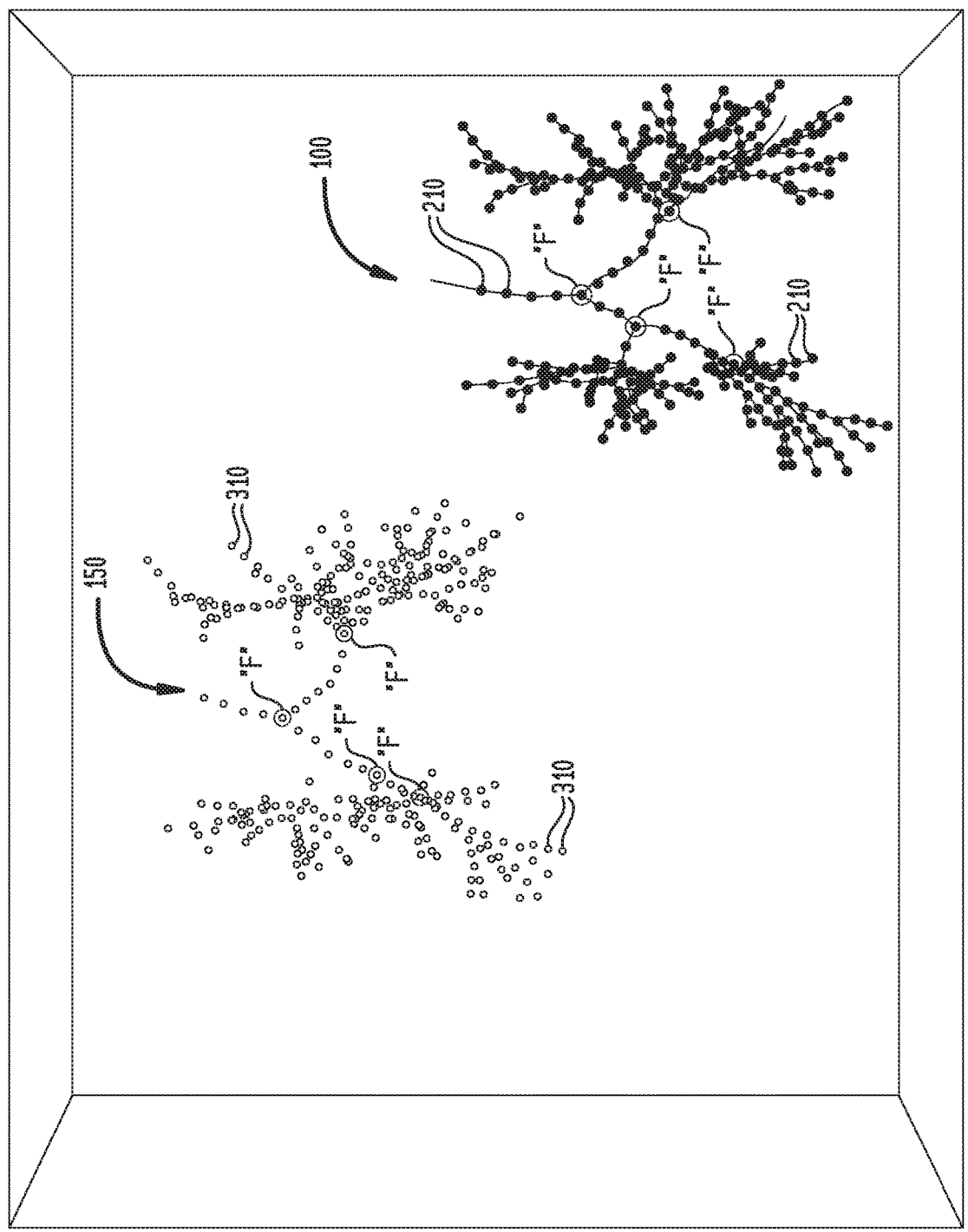
FIG. 1 is an illustration of a CT space and body space, provided in accordance with an embodiment of the present disclosure.

FIG. 1 is an illustration of CT space 100 and body space model 150. CT space 100 is generated from CT scans of a luminal network and is illustrated as a plurality of connected nodes, in the shape of the luminal network. Body space model 150 is illustrated as a point cloud formed by points sensed during EM navigation of the luminal network. As illustrated in FIG. 1, CT space 100 includes plurality of reference points 210, and body space 150 includes plurality of survey points 310. Plurality of reference points 210 are selected from the 3D model of the patient's airways, as further described in the detailed description of FIG. 2, and plurality of survey points 310 are obtained during electromagnetic navigation as further described in the detailed description of FIG. 3. Plurality of reference points 210 and plurality of survey points 510 include x, y, and z coordinates, which indicate the three-dimensional location of each point. Although Cartesian coordinates are used in the present disclosure for simplicity, it is contemplated that a different coordinate system can be used, such as spherical coordinates, cylindrical coordinates, or other coordinate systems. Such other coordinate systems are contemplated to be within the scope of the present disclosure.

Although the present disclosure relates more particularly with electromagnetic navigation and registration and using a plurality of survey points 310 obtained during electromagnetic navigation, which are mapped with a 3D model generated from a CT scan, it is contemplated that plurality of survey points 310 may obtained via ultrasound, fluoroscopic, and magnetic resonance imaging modalities or other imaging means, which allow a processor or other sensors to determine the location of targets and areas within the patient's airways.

In contrast to the registration disclosed in "AUTOMATIC REGISTRATION TECHNIQUE," which is known as rigid, the present disclosure provides registration accuracy by incorporating the flexibility of the lungs into the registration via various interpolation techniques, and is herein referred to as "non-rigid" registration. Before describing non-rigid registration, the TPS transformation will now be described. The TPS transformation maps the plurality of reference points 210 (CT space) and plurality of survey points 310 (body space) in a manner that permits interpolation of additional points in each space. Points in the CT space are denoted as $X_i=(X_i, Y_i, Z_i)$, and points in the body space are denoted as $x_i=(x_i, y_i, z_i)$. Pairs of points in the CT space and in the body space that are associated with each other by the TPS Transform are defined as $\{(x, X)\}=\{(x_i, y_i, z_i),(X_i, Y_i, Z_i)\}$, for i=1, N, where N is the number of reference point 210 and survey point 310 pairs. As further described herein, using a TPS Transform, each survey point from set $\{x\}$, defining a plurality of survey points 310, are paired with each reference point from set $\{x\}$, defining a plurality of reference points 210. The TPS Transform is a transformation which maps plurality of reference points 210 to plurality of survey points 310.

Certain reference points and survey points are selected as fiducial points "F" from the body space and the CT space. Fiducial points "F" are selected from plurality of reference points 210 and plurality of survey points 310, for example, at intersections in the airways where the airway branches apart. Fiducial points "F" provide an initial pairing of plurality of survey points 310 with plurality of reference points 210 that can be relatively easily identified due to their locations within the physiology of the patient. Matching is constructed between all fiducial points "F" in the Body space and the CT space 100, 150 and filtering may be used to eliminate incorrect matches between fiducial points "F" which are too distant to be proper matches. Furthermore, using a process referred to herein as multi-rigid registration, which is explained in more detail below in connection with FIGS. 2 and 3, further pairs of points can be identified and used to derive the TPS Transformation. In determining the pairing between plurality of survey points 310 and plurality of reference points 210, it is contemplated that survey points 310 and reference points 210 which are located at the terminal ends are not paired or matched.

Following matching of the reference points 210 and survey points 310, the TPS Transformation may be derived. The TPS Transform between survey point $x_i=(x_i, y_i, z_i)$ and reference point $X_i=(X_i, Y_i, Z_i)$ is given by the following equation:

$$X_i=\Sigma_{k=1}^{N} w_k \psi(\|x_i-x_k\|)+p(x_i), \quad (1)$$

where $$p(x_i)=a_0+a_1 x_i+a_2 y_i+a_3 z_i \quad (2)$$

$w_k$ are weights and $a_{0\ldots 3}$ are coefficients corresponding to the linear portion of the transformation. Deriving the TPS Transform involves determining the values $w_k$ and $a_{0\ldots 3}$ that satisfy equations (1) and (2), given the known pairs of points $\{(x, X)\}$, and given the further constraints shown in equations (3) and (4):

$$\begin{pmatrix} B+\lambda I & Q \\ Q^T & 0 \end{pmatrix} \begin{pmatrix} w \\ a \end{pmatrix} = \begin{pmatrix} f \\ 0 \end{pmatrix} \qquad (3)$$

$$B_{ij} = \psi(\|x_i - x_j\|), Q_{i,1\ldots 4} = \{1, x_i, y_i, z_i\}, \lambda > 0 \qquad (4)$$

where $\lambda$ is a smoothness parameter, which determines how close reference points 310 have to be mapped to survey points 310, I is a matrix of values 1 to N, w is a matrix of values $w_k$, a is the matrix of values $a_0 \ldots _3$, and $\psi(\ )$ is some function. The value of A depends on the noise level in the data and the number of reference points, and usually is a small number of the order of 0.05. In various embodiments, the value of the smoothness parameter can be in the range between 0 and 10/n, where n is the number of reference point-survey point pairs.

Figure 2:
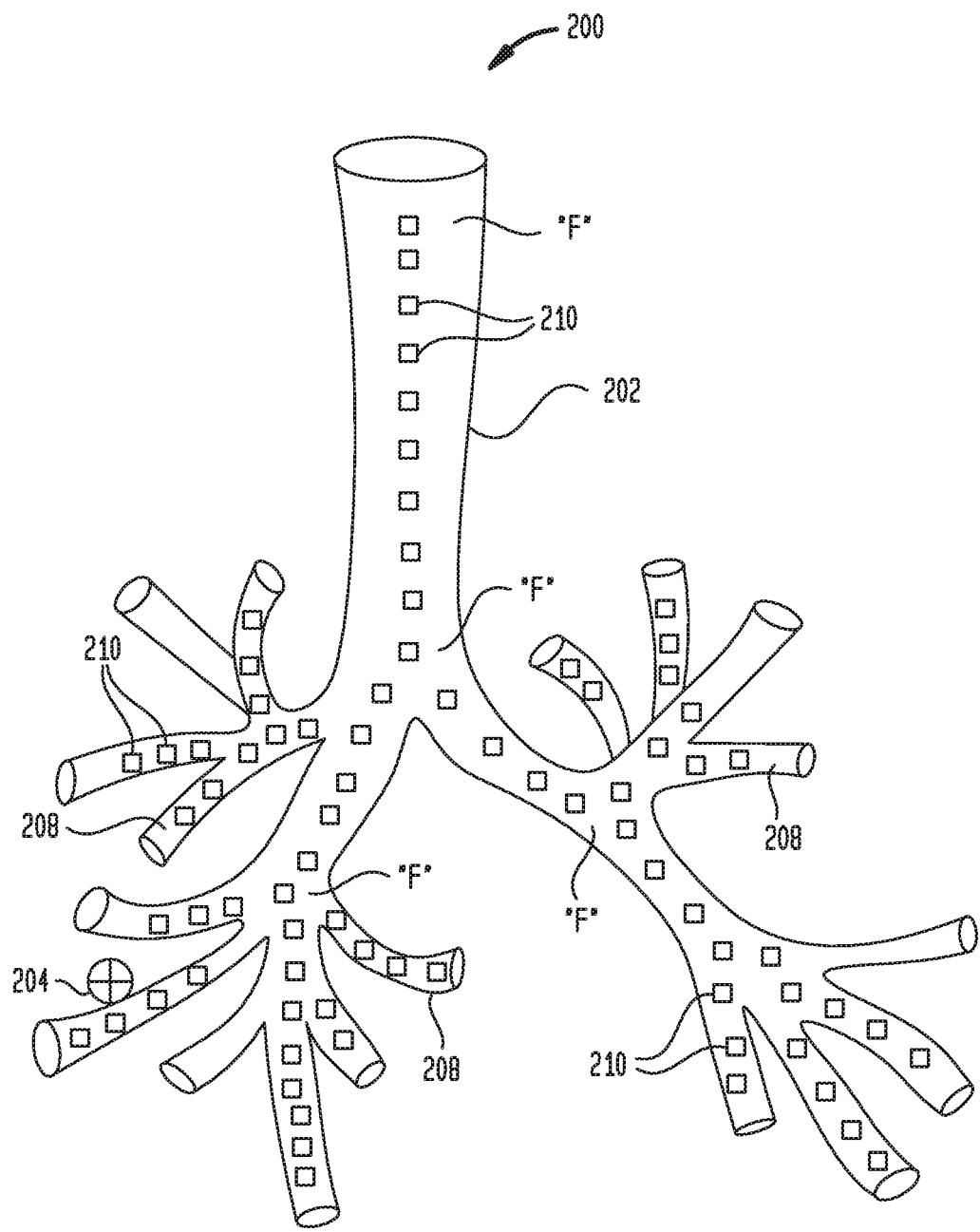
FIG. 2 is a view of a 3D model of the airways based on the CT scans of a patient provided in accordance with an embodiment of the present disclosure.
Figure 6:
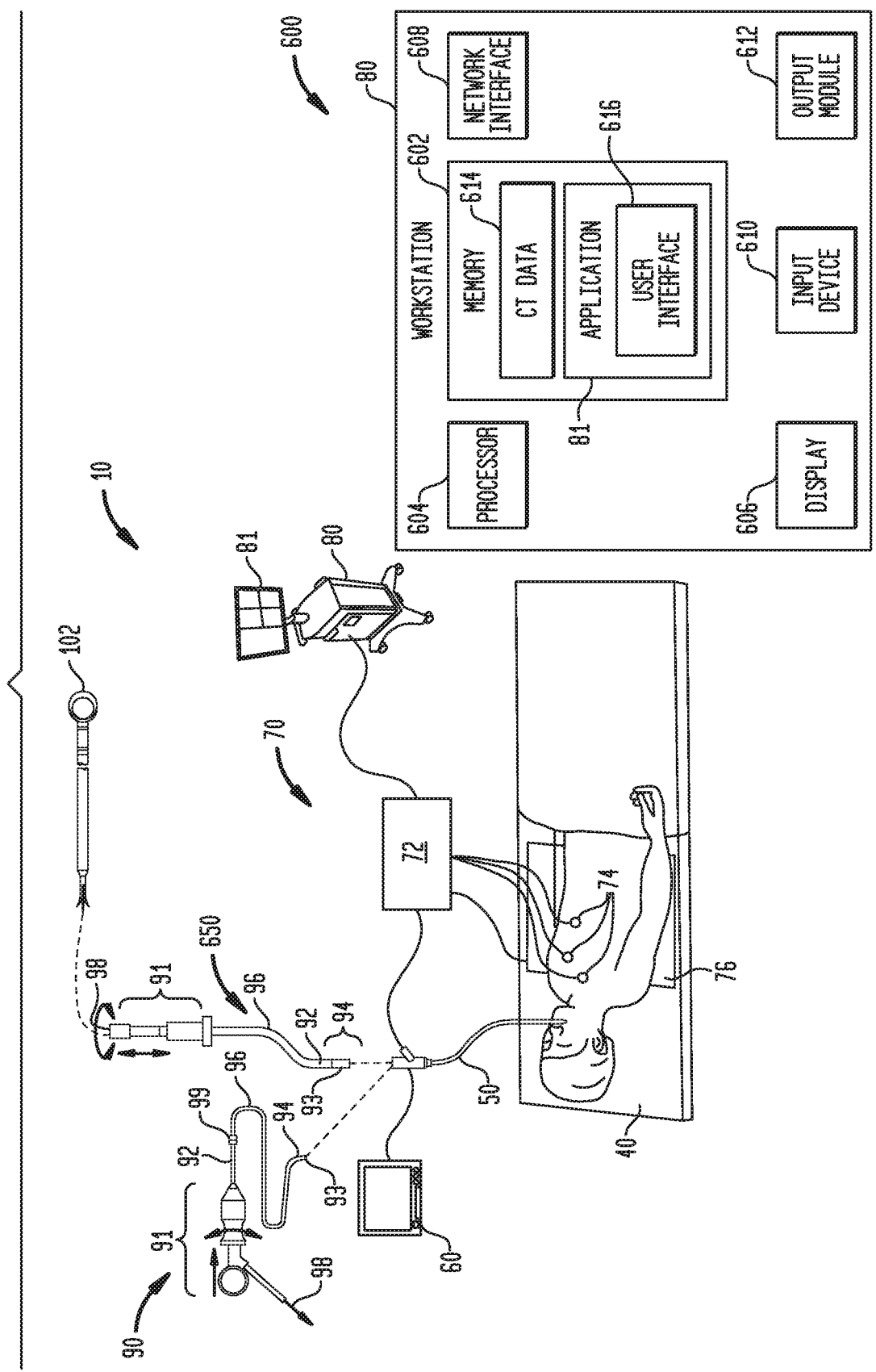
FIG. 6 is a perspective view of an electromagnetic navigation system and a schematic diagram of a workstation, provided in accordance with an embodiment of the present disclosure

Turning now to FIG. 2, a 3D model of a patient's airways created based on a CT scan is illustrated. As shown in FIG. 2, 3D model 200 of the patient's airways includes airway tree 202, one or more targets 204, and airway branches 208 originating from the bifurcations in airway tree 202. Additionally, included within 3D model 200 is plurality of reference points 210 and fiducial points "F." Plurality of reference points 210 are selected at location within the center of the airways of 3D model 200, and each includes x, y, and z coordinates which are recorded and stored in memory 602 (FIG. 6). Further, the reference points 210 are selected at predetermined distance intervals throughout airway tree 402 and airway branches 408. In closer proximity to one or more targets 204 the predetermined distance intervals may be decreased thus increasing the number of reference points 210. Once all reference points 210 are selected, CT space 100 illustrated in FIG. 1 may be creating by plotting all locations of plurality of reference points 210.

Figure 3:
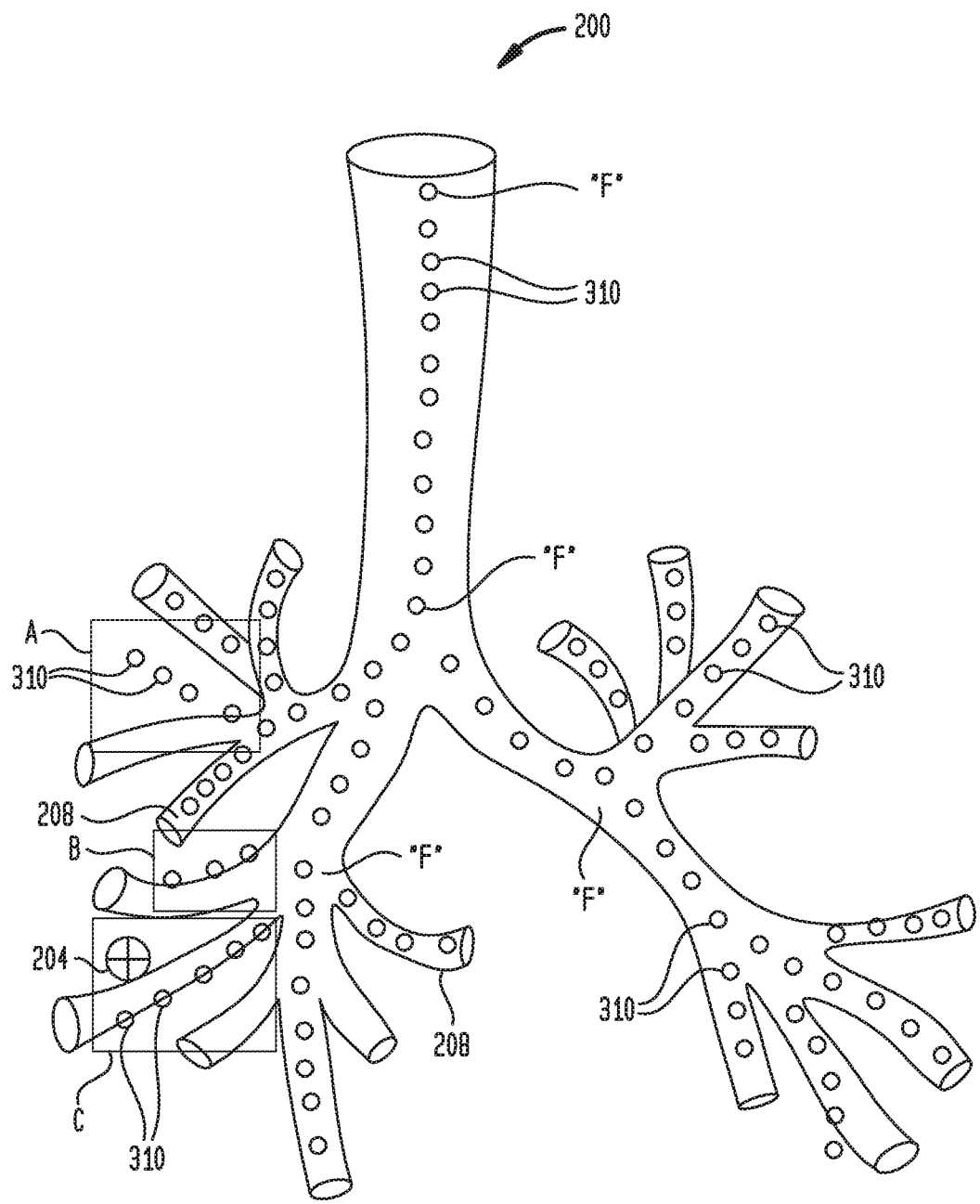
FIG. 3 a view of the 3D model of FIG. 2 together with survey points obtained from electromagnetic navigation of the airways, provided in accordance with an embodiment of the present disclosure.

Referring now to FIG. 3, there is shown plurality of survey points 310 and fiducial points "F" overlaid over the 3D model of airway tree 200 and airway branches 208 from the CT space of FIG. 2. As illustrated in FIG. 3, some survey points 310, particularly those located within areas A, B, and C, are located outside of the 3D model 200 and airway branches 208 when they are converted to the CT space. Survey points 310 are obtained during electromagnetic navigation. During electromagnetic navigation, EM sensor 94 and/or surgical tool 102, in conjunction with tracking system 70, enables tracking of EM sensor 94 and/or surgical tool 102 (FIG. 6) as it is advanced through the patient's airways. EM sensor 94 may be incorporated into surgical tool 102 or different types of tools, such as a biopsy tool, microwave ablation tool, surgical stapling tools, radiotherapy ink application tools, etc., and enables determination of the current location of the tools. As EM sensor 94 and/or surgical tool 102 is advanced through the patient's airways, the x, y, and z coordinates of EM sensor 94 and/or surgical tool 102 are obtained at predetermined distance intervals and are stored in memory 602 (FIG. 6). In closer proximity to one or more targets 204, the predetermined distance intervals may be decreased, thus increasing the number of plurality of survey points 310 obtained. Following an electromagnetic navigation, all survey points 310 are obtained, and the body space 150 illustrated in FIG. 1 may be created by plotting the locations of plurality of survey points 310.

Figure 4:
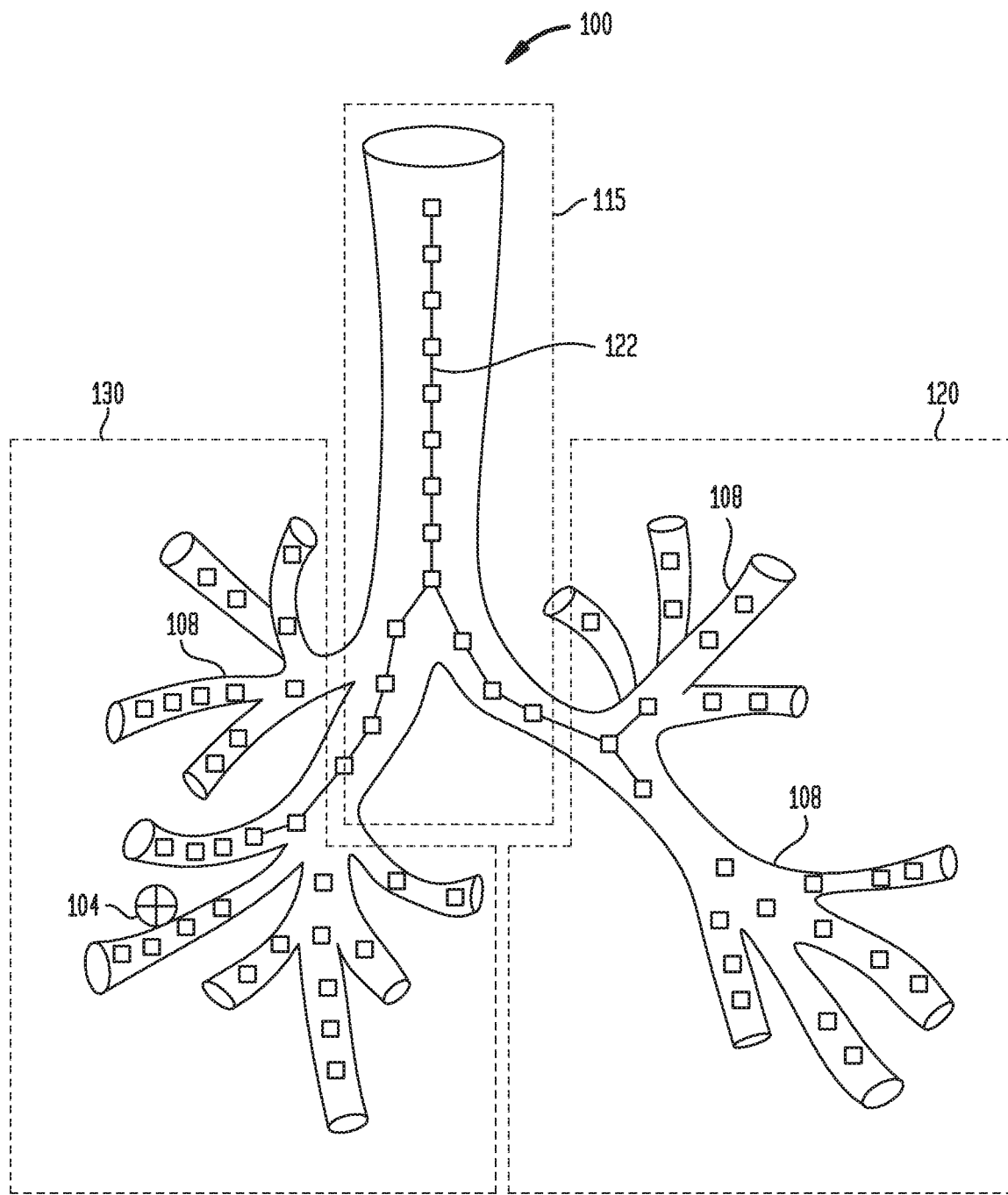
FIG. 4 is a view of the 3D model of the airways of FIGS. 2 and 3 showing designated airway regions, provided in accordance with an embodiment of the present disclosure.

As further shown in FIG. 3, when survey points 310 located in areas A, B, and C are converted to the CT space, they become outside of the 3D model 200 and airway branches 208 in certain locations, indicating that the body space is not accurately registered with 3D model 200 in those areas. As described above, more accurate antenna-to-CT registration can be accomplished using non-rigid registration, which includes multi-rigid registration and the TPS Transform. Multi-rigid registration is described below in connection with FIG. 4. It is contemplated that other types of registration and inverse registration other than multi-rigid registration can be used and are within the scope of the present disclosure. Referring now to FIG. 4, there is shown, in connection with multi-rigid registration, an illustration of 3D model 100 of a patient's airways generated based on a computed tomographic (CT) scan. As shown in FIG. 4, 3D model 100 includes an airway tree 122, target 104, and airway branches 108. 3D model 100 is divided into a plurality of regions. Central region 115 includes the trachea and surrounding airways, left lung region 120 includes the airways of the left lung, and right lung region 130 includes the airways of right lung. In multi-rigid registration, each of the plurality of regions is associated with a separate registration. For example, in one embodiment, central region 115, left lung region 120, and right lung region 130 each will have a separate registration. The number of regions and the location and arrangement of regions is exemplary, and other numbers, locations, and arrangement of regions are contemplated to be within the scope of the present disclosure. For example, a particular arrangement of regions can include a region for a target lobe region, a region for the other lobe, and transition regions to the lobes. Other arrangements are contemplated.

As used herein, multi-rigid registration refers to a collection of optimized region registrations. As explained below, optimized region registration seeks to align a particular region of a reference airway tree as closely as possible with the corresponding region of the survey airway tree, while taking into account to a lesser extent the overall alignment of other regions of the airway tree. Optimized region registration is performed for each region of the airway tree, and this entire process is referred to as multi-rigid registration.

During multi-rigid registration and optimized region registration, as further described herein, it is contemplated that each of the plurality of regions will have weight assigned, which is used to determine the amount that each region of reference airway tree 122 is able to be aligned with the corresponding region of survey airway tree 200. The weight assigned to each of the plurality of regions is also applied to plurality of survey points 310 located within that region, as explained below. During multi-rigid registration/optimized region registration, different regions of the airway tree are weighted differently such that regions with larger weights are favored in the process of aligning the survey airway tree 150 and the reference airway tree 122. For example, suppose a survey airway tree has two regions A and B, and the region weights are 0.9 for region A and 0.1 for region B. The weight of 0.9 is distributed evenly across all survey points of region A, and the weight of 0.1 is distributed evenly across all survey points of region B. For example, if region A has three (3) survey points, then each survey point in region A is assigned a weight of 0.9/3=0.3, and if region B has two (2) survey points, then each survey point in region B is assigned a weight of 0.1/2=0.05. A metric referred to as "divergence" is calculated in which the minimum distance from each survey point to a prospective transformation of the reference airway tree is multiplied by the weight assigned to the corresponding survey point, and the weighted minimum distances are averaged. Thus, the divergence is essentially a weighted average of the minimum distances, where survey points having greater weight will have a greater effect on the divergence. The divergence metrics for prospective transformations are compared, and the transformation corresponding to the minimum divergence is selected as the transformation to use. As explained above, this process for a particular region is referred to as optimized region registration. The result of an optimized region registration is a particular registration that closely aligns the survey airway tree with the reference airway tree in the particular region. Thus, when there are multiple regions, optimized region registration is performed for each region, and the result is several separate registrations. The entire process of performing optimized region registration for all of the regions is what is referred to herein as multi-rigid registration. The particular way of determining divergence described above is exemplary, and other ways of determining divergence are contemplated to be within the scope of the present disclosure.

As mentioned above, multi-rigid registration enables identification of additional pairs of points in the CT space and in the body space for use in deriving the TPS Transform. Multi-rigid registration is what is referred to in the art as antenna-to-CT registration, which is a mechanism to convert coordinates in the body space to coordinates in the CT space. This mechanism can be inverted so that coordinates in the CT space can be converted to coordinates in the body space. In various embodiments, inverse multi-rigid registration can be used to identify additional pairs of points for deriving the TPS Transform. Starting with the reference points 210 in the CT space and applying the inverse multi-rigid registration to them, corresponding points in the body space can be determined to form point pairs for deriving the TPS Transform using equations (1) through (4). Although multi-rigid registration has been described, it is contemplated that other types of registrations and inverse registrations can be used to identify pairs of reference points and survey points, and they are within the scope of the present disclosure.

Figure 5:
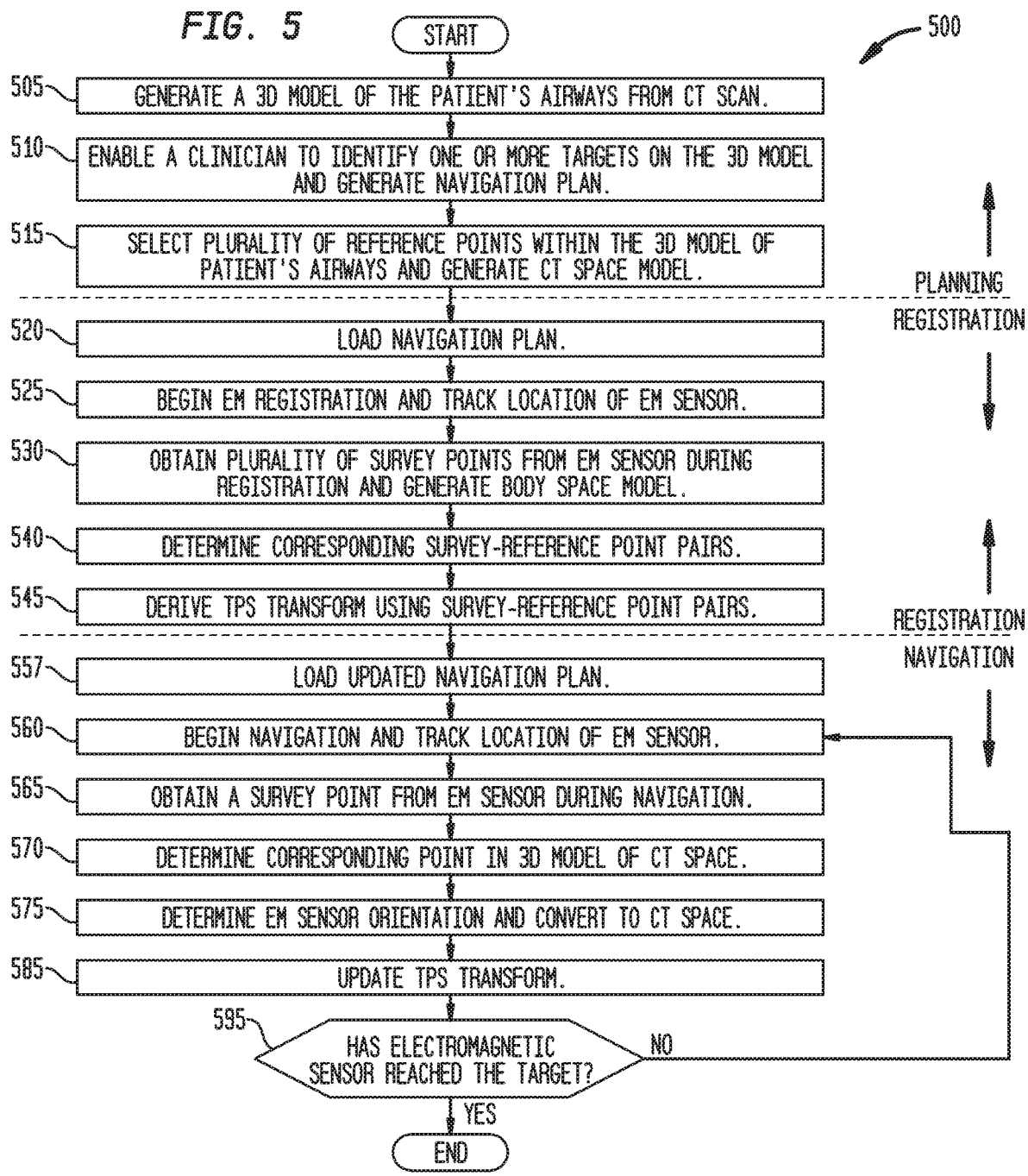
FIG. 5 is a flowchart of a method of electromagnetic registration of a luminal network to a 3D model of the luminal network, provided in accordance with an embodiment of the present disclosure.

FIG. 5 illustrates a flowchart of method 500 detailing operations in accordance with the disclosures herein. Method 500 may be implemented, at least in part, by the processor 604 executing instructions stored in the memory 602 (FIG. 6). Additionally, the particular sequence of steps shown in method 500 is provided by way of example and not limitation. Thus, the steps of method 500 may be executed in sequences other than the sequences shown in FIG. 5 without departing from the scope of the present disclosure. Further, some steps shown in method 500 may be concurrently executed with respect to one another instead of sequentially executed with respect to one another.

As further described herein, method 500 details planning (steps 505-515), registration (steps 520-545), and navigation (steps 557-595) in accordance with aspects of the present disclosure. At step 505, images from a CT scan, taken of a patient, are obtained and a 3D model, such as 3D model 200, of the patient's airways is generated based on the patient's CT scan and, at step 510, the clinician identifies one or more targets, such as one or more targets 204, on 3D model 200 and generates a navigation plan based on 3D model 200. Next, at step 515, plurality of reference points 210 within 3D model 200 is selected, as shown in FIG. 2 and results in generated CT space model 100.

Next, at steps 520-545, electromagnetic registration is performed. At step 520 the navigation plan generated at step 510 is loaded. Next, at step 525, navigation is performed within the patient's airway and the location of EM sensor 94 and/or surgical tool 102 is tracked as it is advanced through the patient's airways. Next, at step 530, processor 604, based on the location of EM sensor 94 and/or surgical tool 102, obtains plurality of survey points 310 within body space 150 within the patient's airways during navigation.

Next, at step 540, utilizing processor 604, and using fiducial points "F" and using inverse multi-rigid registration, corresponding survey-reference point pairs are determined, as described in the detailed description above herein. Following step 540, processor 604 utilizes the survey-reference point pairs to derive the TPS Transform at step 545.

Next, at steps 557-595, navigation and updating of the 3D model during the surgical procedure is performed. As described below, for navigation during the surgical procedure, the TPS Transform can be updated while navigation is in progress. It is contemplated that the EM registration, at steps 525-545, and the navigation during the surgical procedure, at step 557-595, may be done at different times.

At step 557, the clinician loads the navigation plan based on 3D model 200. The navigation plan includes one or more targets 204. Thereafter, the clinician loads the navigation plan into application 81 from memory 602, a USB device, or from network interface 608, as shown in FIG. 6. The navigation plan may require that all or only some regions of the patient's lungs be registered, as described at steps 520-545. Following loading the navigation plan, navigation is performed within the patient's airways towards one or more targets 204 and the location of EM sensor 94 and/or surgical tool 102 is tracked as it is advanced through the patient's airways, at step 560.

At step 565, based on the location of EM sensor 94 and/or surgical tool 102, a survey point 310 within the patient's airways, is obtained in the body space. Next, at step 570, a point in the CT space corresponding to the obtained survey point 310 is determined by applying the TPS Transform of equation (1) to the survey point. In this manner, the location of the EM sensor 94 and/or surgical tool 102 in the CT space can be determined and visualized to assist with real-time navigation.

In addition to determining the location of the sensor 94 and/or surgical tool 102 in the CT space, the orientation of the EM sensor 94 and/or surgical tool 102 can also be determined, at step 575. The orientation of EM sensor 94 may be represented by three orthogonal vectors from survey point 310, where the sum of the three vectors indicates the heading of the EM sensor 94 and/or surgical tool 102. To convey this information from the body space to the CT space using the TPS Transform, the three vectors can be converted into points. Processor 604 generates three points $310x$, $310y$, $310z$ in the body space (not shown), with each point generated by adding one of the three vectors to the survey point 210. Next, by applying the TPS Transform to these three points $310x$, $310y$, $310z$, the corresponding points $210x$, $210y$, and $210z$ in the CT space can be determined. Next, the reference point 210 corresponding to the survey point 310 can be subtracted from each of the points $210x$, $210y$, and $210z$ in the CT space to obtain the three orientation vectors within the CT space. The three orientation vectors in the CT space may not be orthogonal to each other because they were provided by a transform from the body space. Using singular value decomposition, the non-orthogonality of the resulting three orientation vectors within the CT space can be corrected. As understood by persons skilled in the art, such correction is performed by choosing the columns of the U-matrix of singular value decomposition to be the new orthogonal orientation vectors in the CT space.

At step 585, the method can optionally update the TPS Transform. In various embodiments, as survey points are gathered at step 565 in a particular region, the method may have a sufficient number of new survey points to perform a multi-rigid registration to improve the registration of the body space to the CT space in the particular region. Then, the inverse multi-rigid registration can identify pairs of reference points and survey points, which can be used to update the TPS Transform.

At step 595, a determination is made of whether one or more targets 204 have been reached as EM sensor 94 and/or surgical tool 102 is advanced through the patient's airways. If it is determined that EM sensor 94 and/or surgical tool 102 has not reached one or more targets 204, method 500 returns to step 560. If, at step 595, it is determined that EM sensor 94 and/or surgical tool 102 has reached one or more targets 204, method 500 ends.

Referring now to FIG. 6, electromagnetic navigation system 10 is provided in accordance with the present disclosure. One such electromagnetic navigation system is the ELECTROMAGNETIC NAVIGATION BRONCHOSCOPY® system currently sold by Medtronic PLC. Among other tasks that may be performed using electromagnetic navigation system 10 are planning a pathway to target tissue, navigating a positioning assembly to the target tissue, navigating a biopsy tool to the target tissue to obtain a tissue sample from the target tissue using the biopsy tool, digitally marking the location where the tissue sample was obtained, and placing one or more echogenic markers at or around the target.

Electromagnetic navigation system 10 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic (EM) field generator 76; a workstation 80 including software and/or hardware used to facilitate pathway planning, identification of target tissue, navigation to target tissue, and digitally marking the biopsy location FIG. 6 also depicts two types of catheter guide assemblies 90, 650. Both catheter guide assemblies 90, 650 are usable with electromagnetic navigation system 10 and share a number of common components. Each catheter guide assembly 90, 650 includes a handle 91, which is connected to an extended working channel (EWC) 96. EWC 96 is sized for placement into the working channel of a bronchoscope 50. In operation, a locatable guide (LG) 92, including an EM sensor 94, is inserted into EWC 96 and locked into position such that sensor 94 extends a desired distance beyond a distal tip 93 of EWC 96. The location of EM sensor 94, and thus the distal end of EWC 96, within an EM field generated by EM field generator 76 can be derived by tracking module 72, and workstation 80. Catheter guide assemblies 90, 650 have different operating mechanisms, but each contain a handle 91 that can be manipulated by rotation and compression to steer distal tip 93 of LG 92 and EWC 96. Catheter guide assemblies 90 are currently marketed and sold by Medtronic PLC under the name SUPERDIMENSION® Procedure Kits. Similarly, catheter guide assemblies 650 are currently sold by Medtronic PLC under the name EDGE™ Procedure Kits. Both kits include a handle 91, EWC 96, and LG 92. For a more detailed description of the catheter guide assemblies 90, 650, reference is made to commonly-owned U.S. Patent Publication Serial No. US 2014/0046315, entitled MICROWAVE ABLATION CATHETER AND METHOD OF UTILIZING THE SAME, filed on Mar. 15, 2013, by Ladtkow et al., the entire contents of which are hereby incorporated by reference.

As illustrated in FIG. 6, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 650 including LG 92 and EWC 96 are configured for insertion through a working channel of bronchoscope 50 into the patient's airways (although the catheter guide assemblies 90, 650 may alternatively be used without bronchoscope 50). LG 92 and EWC 96 are selectively lockable relative to one another via a locking mechanism 99. Tracking system 70 is configured for use with catheter guide assemblies 90, 650 to track the position of EM sensor 94 as it moves in conjunction with EWC 96 through the airways of the patient, as detailed below.

Electromagnetic field generator 76 is positioned beneath the patient. Electromagnetic field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to workstation 80, which includes and application 81 which uses data collected by sensors 74 to calculate a patient coordinate frame of reference.

Also shown in FIG. 6 is a surgical instrument 102 that is insertable into catheter guide assemblies 90, 650 following navigation to a target and removal of LG 92. Surgical tool 102 may include and is not limited to, tissue collection tool, microwave ablation tool, surgical stapling tools, radiotherapy ink application tools, and the like. Surgical tool 102 is further configured for use in conjunction with tracking system 70 to facilitate navigation of surgical tool 102 to the target tissue, tracking of a location of surgical tool 102 as it is manipulated relative to one or more targets 204.

During procedure planning, workstation 80 utilizes computed tomographic (CT) image data for generating and viewing the 3D model of the patient's airways, enables the identification of target tissue on the 3D model (automatically, semi-automatically or manually), and allows for the selection of a pathway through the patient's airways to the target tissue. More specifically, the CT scans are processed and assembled into a 3D volume, which is then utilized to generate the 3D model of the patient's airways. The 3D model may be presented on a display monitor associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show marks of the locations where previous biopsies were performed, including the dates, times, and other identifying information regarding the tissue samples obtained. These marks may also be selected as the target to which a pathway can be planned. Once selected, the pathway is saved for use during the navigation procedure. Examples of a suitable pathway planning system and method is described in U.S. Patent Application Publication Nos. US 2014/0281961, US 2014/0270441, and US 2014/0282216, all entitled PATHWAY PLANNING SYSTEM AND METHOD, filed on Mar. 15, 2013, by Baker, the entire contents of each of which is incorporated herein by reference.

System diagram 600 of workstation 80 includes memory 602, processor 604, display 606, network interface 608, input device 610, and/or output module 612. Memory 602 includes any non-transitory computer-readable storage media for storing data and/or software that is executable by processor 604 and which controls the operation of workstation 80. In an embodiment, memory 602 may include one or more solid-state storage devices such as flash memory chips. Alternatively or in addition to the one or more solid-state storage devices, memory 602 may include one or more mass storage devices connected to the processor 604 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 604. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

Memory 602 may store application 81 and/or CT data 614. Application 81 may, when executed by processor 604, cause display 606 to present user interface 616. Network interface 208 may be configured to connect to a network such as a local area network (LAN) consisting of a wired network and/or a wireless network, a wide area network (WAN), a wireless mobile network, a Bluetooth network, and/or the internet. Input device 510 may be any device by means of which a user may interact with workstation 50, such as, for example, a mouse, keyboard, foot pedal, touch screen, and/or voice interface. Output module 612 may include any connectivity port or bus, such as, for example, parallel ports, serial ports, universal serial busses (USB), or any other similar connectivity port known to those skilled in the art.

Memory 602 includes any non-transitory computer-readable storage media for storing data and/or software that is executable by processor 604 and which controls the operation of workstation 80. In an embodiment, memory 602 may include one or more solid-state storage devices such as flash memory chips. Alternatively or in addition to the one or more solid-state storage devices, memory 602 may include one or more mass storage devices connected to the processor 604 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 604. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

What is claimed is:

1. A system comprising:
   a location sensor capable of being navigated within a luminal network inside a patient's body;
   an electromagnetic field generator configured to detect a location of the location sensor as it is navigated within the luminal network;
   a computing device including a processor and a memory; and
   an application, stored in the memory and executed by the processor, which when executed, causes the computing device to:
   during a planning phase:
      receive a 3D model of the luminal network, the 3D model being generated from computed tomographic (CT) images of the luminal network, the 3D model corresponding to a CT coordinate space;
      generate a navigation plan; and
      select, at predetermined distance intervals, a plurality of reference points within the 3D model of the luminal network, the reference points being along a center of the luminal network of the 3D model;
   during a registration phase:
      receive a plurality of survey points within the luminal network, the plurality of survey points corresponding to a body coordinate space and being based on locations of the location sensor while the location sensor is navigated within the luminal network;
      correlate the plurality of survey points with the plurality of reference points to determine pairs of correlated reference points and survey points; and
      derive a thin plate splines (TPS) transformation that maps the body coordinate space to the CT coordinate space based on the pairs of correlated reference points and survey points by interpolating additional points in the body coordinate space and the CT coordinate space based on an inverse multi-rigid registration, yielding a derived TPS transformation;
   during a navigation phase different from the registration phase:
      receive a further survey point from the location sensor, which is navigated according to the navigation plan;
      determine a location of the location sensor in the CT coordinate space by determining a point in the 3D model corresponding to the further survey point by applying the derived TPS transformation to the further survey point; and
      update the derived TPS transformation based on a plurality of second additional correlated points interpolated from the inverse multi-rigid registration performed on the further survey point while navigation is in progress.

2. The system of claim 1, wherein the luminal network is an airway of a patient.

3. The system of claim 2, wherein the 3D model is a model of the airway of the patient.

4. The system of claim 1, wherein the application stored in the memory when executed, further causes the computing device to:
   select fiducial points from the plurality of survey points and the plurality of reference points, wherein the fiducial points are at intersections in the luminal network where the luminal network branches apart.

5. The system of claim 4, wherein in correlating the plurality of survey points with the plurality of reference points, the application stored in the memory when executed, further causes the computing device to:
 match the fiducial points selected from the plurality of survey points with the fiducial points selected from the plurality of reference points, yielding matched fiducial points, wherein the pairs of correlated reference points and survey points include the matched fiducial points.

6. The system of claim 1, wherein correlating the plurality of survey points with the plurality of reference points is based on an inverse registration of the CT coordinate space to the body coordinate space.

7. The system of claim 6, wherein the inverse registration is at least one of: an inverse of an optimized zone registration or an inverse of a multi-rigid registration.

8. The system of claim 1, wherein the application stored in the memory, when executed, further causes the computing device to update the derived TPS transformation during the navigation phase by:
 receiving a plurality of further survey points;
 determining a registration of the body coordinate space to the CT coordinate space based on the plurality of further survey points;
 matching the plurality of further survey points with the plurality of reference points based on the registration; and
 updating the derived TPS transformation based on the matching.

9. A system comprising:
 a computing device including a processor and a memory; and
 an application, stored in the memory and executed by the processor, which when executed, causes the computing device to:
 during a planning phase:
  receive a 3D model of a luminal network inside a patient's body, the 3D model being generated from computed tomographic (CT) images of the luminal network and corresponding to a CT coordinate space;
  generate a navigation plan; and
  select, at predetermined distance intervals, a plurality of reference points within the 3D model of the luminal network, the reference points being along a center of the luminal network of the 3D model;
 during a registration phase:
  receive a plurality of survey points within the luminal network, the plurality of survey points corresponding to a body coordinate space and being based on locations of a location sensor while the location sensor is navigated within the luminal network;
  correlate the plurality of reference points and the plurality of survey points to determine a plurality of correlated points;
  perform an inverse multi-rigid registration of the CT coordinate space to the body coordinate space based on the plurality of correlated points;
  interpolate a plurality of additional correlated points based on the inverse multi-rigid registration; and
  derive a TPS transformation that maps the body coordinate space to the CT coordinate space from the plurality of correlated points and the plurality of additional correlated points, yielding a derived TPS transformation; and
 during a navigation phase different from the registration phase:
  receive a further survey point from the location sensor, which is navigated according to the navigation plan;
  determine a location of the location sensor in the CT coordinate space by determining a point in the 3D model corresponding to the further survey point by applying the derived TPS transformation to the further survey point; and
  update the derived TPS transformation based on a plurality of second additional correlated points interpolated from the inverse multi-rigid registration performed on the further survey point while navigation is in progress.

10. A system comprising:
 a computing device including a processor and a memory; and
 an application, stored in the memory and executed by the processor, which when executed, causes the computing device to:
 during a planning phase:
  receive a 3D model of a luminal network inside a patient's body, the 3D model being generated from computed tomographic (CT) images of the luminal network and corresponding to a CT coordinate space;
  generate a navigation plan; and
  select, at predetermined distance intervals, a plurality of reference points within the 3D model of the luminal network, the reference points being along a center of the luminal network of the 3D model;
 during a registration phase:
  receive a plurality of survey points within the luminal network, the plurality of survey points being based on electromagnetic navigation data and corresponding to a body coordinate space;
  perform an inverse multi-rigid registration of the CT coordinate space to the body coordinate space based on the plurality of reference points and the plurality of survey points; and
  derive a thin plate splines (TPS) transformation that maps the body coordinate space to the CT coordinate space from a plurality of additional points interpolated based on the inverse multi-rigid registration, yielding a derived TPS transformation; and
 during a navigation phase different from the registration phase:
  receive a further survey point from a location sensor, which is navigated according to the navigation plan;
  determine a location of the location sensor in the CT coordinate space by determining a point in the 3D model corresponding to the further survey point by applying the derived TPS transformation to the further survey point; and
  update the derived TPS transformation based on a plurality of second additional correlated points interpolated from the inverse multi-rigid registration performed on the further survey point while navigation is in progress.

11. The system of claim 10, wherein the luminal network is an airway of a patient.

12. The system of claim 11, wherein the 3D model is a model of the airway of the patient.

13. The system of claim 10, further including selecting fiducial points from the plurality of survey points and the plurality of reference points wherein the fiducial points are at intersections in the luminal network where the luminal network branches apart.

14. The system of claim 13, wherein performing the inverse registration includes performing the inverse registration based on the fiducial points.

15. The system of claim 10, wherein performing the inverse registration of the CT coordinate space to the body coordinate space includes correlating the plurality of reference points and the plurality of survey points.

16. The system of claim 10, wherein the inverse registration is at least one of: an inverse of an optimized zone registration or an inverse of a multi-rigid registration.

17. The system of claim 10, wherein the application, when executed, further causes the computing device to update the derived TPS transformation during the navigation phase by:
   receiving a plurality of further survey points;
   determining a registration of the body coordinate space to the CT coordinate space based on the plurality of further survey points;
   matching the plurality of further survey points with the plurality of reference points based on the registration; and
   updating the derived TPS transformation based on the matching.

18. The system of claim 10, further comprising:
   a location sensor capable of being navigated within the luminal network inside the patient's body; and
   an electromagnetic field generator configured to detect the location of the location sensor as it is navigated within the luminal network.

* * * * *